(12) United States Patent
Takama

(10) Patent No.: US 9,084,563 B2
(45) Date of Patent: Jul. 21, 2015

(54) MEDICAL SYSTEM

(71) Applicant: CANON KABUSHIKI KAISHA, Tokyo (JP)

(72) Inventor: Yasufumi Takama, Kawasaki (JP)

(73) Assignee: Canon Kabushiki Kaisha, Tokyo (JP)

( * ) Notice: Subject to any disclaimer, the term of this patent is extended or adjusted under 35 U.S.C. 154(b) by 0 days.

(21) Appl. No.: 14/108,471

(22) Filed: Dec. 17, 2013

(65) Prior Publication Data

US 2014/0111514 A1    Apr. 24, 2014

Related U.S. Application Data

(63) Continuation of application No. 13/231,157, filed on Sep. 13, 2011, now Pat. No. 8,638,992.

(30) Foreign Application Priority Data

Sep. 29, 2010  (JP) .................................. 2010-219765

(51) Int. Cl.
*A61B 3/10*    (2006.01)
*A61B 5/00*    (2006.01)
(Continued)

(52) U.S. Cl.
CPC ............... *A61B 3/102* (2013.01); *A61B 5/0066* (2013.01); *A61B 8/10* (2013.01); *G06T 7/0012* (2013.01); *G06T 11/008* (2013.01); *G06T 15/08* (2013.01); *G06T 19/20* (2013.01); *G06T 2219/2012* (2013.01)

(58) Field of Classification Search
CPC .............. A61F 2009/00851; A61F 2009/0088; A61F 9/00834; A61F 2009/00863; A61F 2009/00882; A61B 3/102; A61B 5/0066; A61B 3/1005; A61B 8/10; A61B 3/10; A61B 19/5212; A61B 3/1015; A61B 5/0073; A61B 6/032; G01B 9/02091; G01B 9/0203; G01B 9/02085; G06T 2207/30041; G06T 15/08; G06T 2207/10101; G06T 2207/10072; G06T 7/0012; G06T 11/008; G06T 19/20; G01N 2021/1787; G01N 23/04

See application file for complete search history.

(56) References Cited

U.S. PATENT DOCUMENTS 5,279,296 A *   1/1994  Thurston et al. ............... 600/372
7,860,284 B2 * 12/2010  Matsumoto .................... 382/128
(Continued)

FOREIGN PATENT DOCUMENTS

JP    2007-209538 A    8/2007
JP    2008-006274 A    1/2008
(Continued)

OTHER PUBLICATIONS

A. Jani, et al., "Opacity Transfer Function Optimization for Volume-rendered Computed Tomography Images of the Prostate", Academic Radiology, Reston, VA, US, vol. 12, No. 6, pp. 761-770.
(Continued)

*Primary Examiner* — Manav Seth
(74) *Attorney, Agent, or Firm* — Fitzpatrick, Cella, Harper & Scinto

(57) ABSTRACT

A medical system comprising a selection unit configured to select at least one of layers in a three-dimensional tomographic image of a retina, and a generation unit configured to generate an opacity function indicating an opacity of each of a plurality of voxels constituting the selected layer, based on a frequency distribution of luminance values of the plurality of voxels.

26 Claims, 8 Drawing Sheets

(51) Int. Cl.
*G06T 11/00* (2006.01)
*G06T 15/08* (2011.01)
*G06T 19/20* (2011.01)
*A61B 8/10* (2006.01)
*G06T 7/00* (2006.01)

(56) References Cited

U.S. PATENT DOCUMENTS

| | | | |
|---|---|---|---|
| 7,940,398 B2* | 5/2011 | Ohbayashi et al. | 356/479 |
| 7,982,879 B2* | 7/2011 | Desjardins et al. | 356/477 |
| 8,085,408 B2* | 12/2011 | Everett et al. | 356/497 |
| 8,401,246 B2* | 3/2013 | Huang et al. | 382/117 |
| 8,638,992 B2* | 1/2014 | Takama | 382/117 |
| 8,687,863 B2* | 4/2014 | Takama | 382/128 |
| 8,699,774 B2* | 4/2014 | Yonezawa et al. | 382/131 |
| 8,705,826 B2* | 4/2014 | Liu et al. | 382/131 |
| 8,744,158 B2* | 6/2014 | Takama et al. | 382/131 |
| 2001/0000978 A1* | 5/2001 | Hitzenberger et al. | 356/484 |
| 2005/0017972 A1 | 1/2005 | Poole et al. | |
| 2007/0183644 A1 | 8/2007 | Matsumoto | |
| 2007/0274583 A1 | 11/2007 | Sugiyama et al. | |
| 2008/0069444 A1 | 3/2008 | Wilensky | |
| 2008/0309881 A1* | 12/2008 | Huang et al. | 351/246 |
| 2010/0189334 A1* | 7/2010 | Tomidokoro et al. | 382/131 |
| 2010/0194757 A1 | 8/2010 | Tomidokoro et al. | |
| 2011/0243408 A1 | 10/2011 | Takama | |
| 2011/0243415 A1* | 10/2011 | Yonezawa et al. | 382/131 |

FOREIGN PATENT DOCUMENTS

| | | |
|---|---|---|
| JP | 2008-086658 A | 4/2008 |
| JP | 2010-142498 A | 7/2010 |
| WO | 2010/071091 A1 | 6/2010 |

OTHER PUBLICATIONS

M. Selver, et al., "A software tool for interactive generation, representation, and systematical storage of transfer functions for 3D medical images", Computer Methods and Programs in Biomedicine, Elsevier, Amsterdam, NL, vol. 86, No. 3, pp. 270-280.

Jan. 30, 2012 European Search Report in European Patent Appln. No. 11180401.9.

* cited by examiner

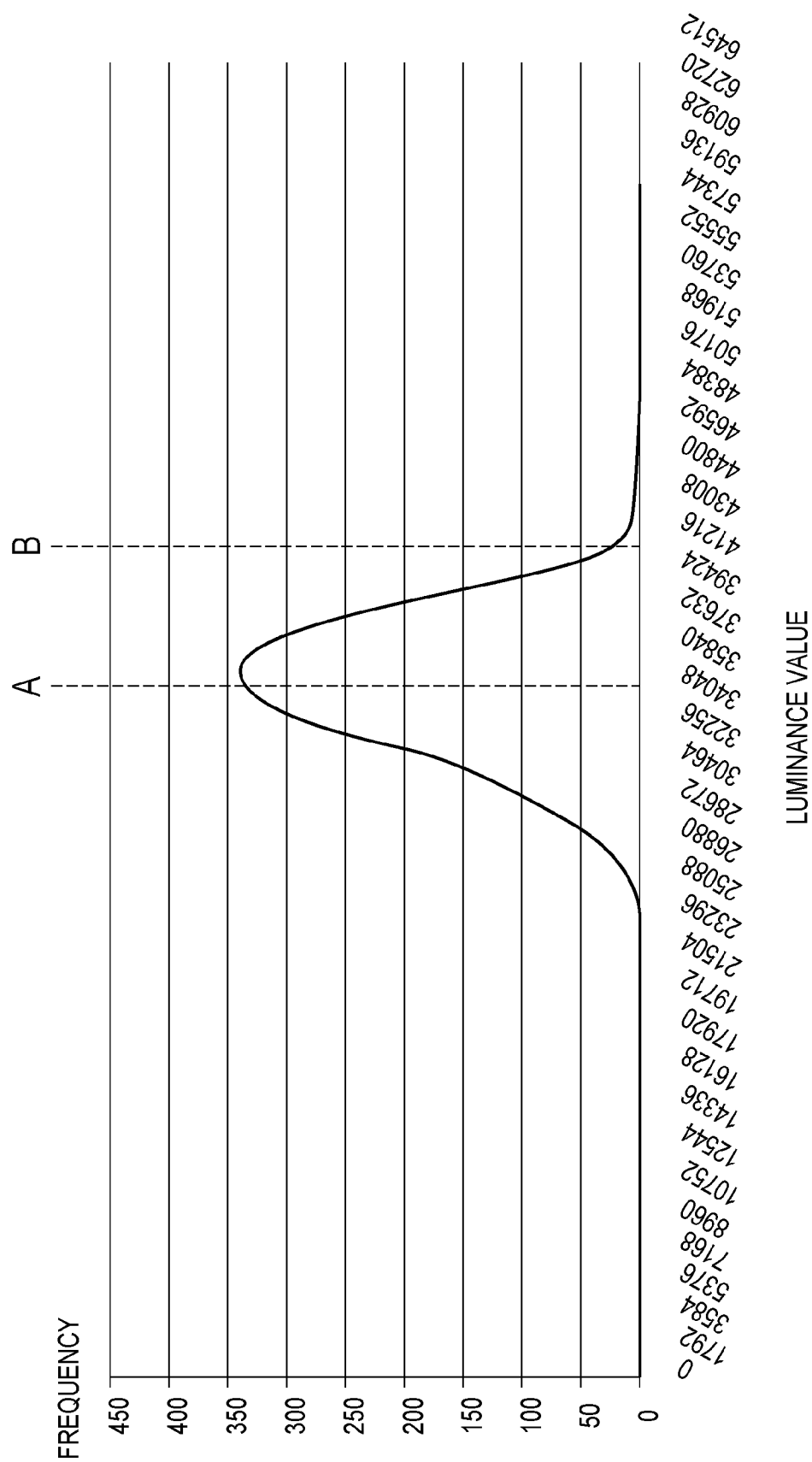

MEDICAL SYSTEM

This application is a continuation of application Ser. No. 13/231,157 filed Sep. 13, 2011.

BACKGROUND OF THE INVENTION

1. Field of the Invention

The present invention relates to a medical system.

2. Description of the Related Art

Recently, in ophthalmic sites, an apparatus called an optical coherence tomography (to be referred to as an OCT hereinafter) has been introduced. This apparatus can obtain a volume image constituted by a plurality of two-dimensional tomographic images of the retina.

In ophthalmic sites, users (technicians and doctors) interpret a layer structure from a volume image and observe the states and distribution of lesions and the three-dimensional running of fundus blood vessels. It is therefore necessary to display the distribution of lesions and blood vessels by using volume images so as to facilitate observation.

As a technique for implementing such a display, volume rendering is known, which assigns opacities to voxels in accordance with an opacity function, and performs translucent display of target volume data, thereby visualizing an internal structure.

In general, the user generates an opacity function by manually setting the shape and the position of a peak, width, and the like of a function by using a user interface. Japanese Patent Laid-Open No. 2008-006274 discloses a technique of automatically generating such an opacity function. This technique fits a Gaussian function to a CT value histogram and can opaquely display the range of CT values calculated from the average value and standard deviation of the resultant data.

In this case, the following problems arise in the arrangement configured to automatically generate an opacity function to perform volume rendering for easy observation of tissues in a volume image of the retina.

Consider a case in which blood vessels are displayed. In this case, in a tomographic image obtained by OCT, the luminance value of a blood vessel region is high. Since a region near the lower end of the nerve fiber layer in which blood vessels run has a high luminance value, the contrast of the region in which blood vessels run is low. This makes it difficult to facilitate observation of blood vessels by volume rendering using an automatically generated opacity function.

Consider a large number of white spots distributed in a layer below the nerve fiber layer and a layer above the retinal pigment epithelium. The luminance values of white spots are high like those of these layers. For this reason, even if the luminance values are converted into opacities, the nerve fiber layer and the retinal pigment epithelium located outside the white spots are displayed, and the white spots located inside them are difficult to display.

When displaying tissues (blood vessels and white spots) of the retina based on a tomographic image captured by OCT in this manner, even if an opacity function is automatically generated, the tissues may not be effectively displayed to the user (technician or doctor).

SUMMARY OF THE INVENTION

The present invention provides a technique of automatically generating an opacity function in accordance with a display target.

According to a first aspect of the present invention there is provided a medical system comprising: a selection unit configured to select at least one of layers in a three-dimensional tomographic image of a retina; and a generation unit configured to generate an opacity function indicating an opacity of each of a plurality of voxels constituting the selected layer, based on a frequency distribution of luminance values of the plurality of voxels.

According to a second aspect of the present invention there is provided a medical system comprising: a selection unit configured to select at least one of layers in a three-dimensional tomographic image of a retina; and a generation unit configured to generate a frequency distribution of luminance values of a plurality of voxels constituting the selected layer.

Further features of the present invention will be apparent from the following description of exemplary embodiments (with reference to the attached drawings).

BRIEF DESCRIPTION OF THE DRAWINGS

The accompanying drawings, which are incorporated in and constitute a part of the specification, illustrate embodiments of the invention, and together with the description, serve to explain the principles of the invention.

FIG. 5A is a graph showing an example of the distribution of luminance values in a selected layer;

DESCRIPTION OF THE EMBODIMENTS

An exemplary embodiment(s) of the present invention will now be described in detail with reference to the drawings. It should be noted that the relative arrangement of the components, the numerical expressions and numerical values set forth in these embodiments do not limit the scope of the present invention unless it is specifically stated otherwise.

(First Embodiment)

Figure 1:
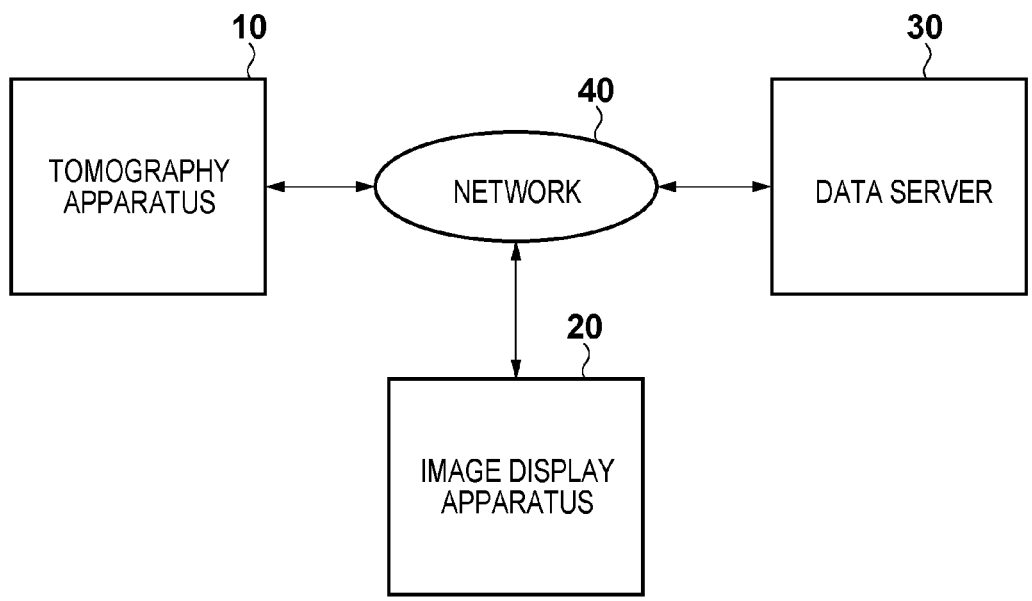
FIG. 1 is a block diagram showing an example of the overall arrangement of a diagnosis support system according to an embodiment of the present invention.

FIG. 1 is a block diagram showing an example of the overall arrangement of a diagnosis support system (medical system) according to an embodiment of the present invention.

A tomography apparatus 10, an image display apparatus 20, and a data server 30 are connected to this diagnosis support system via a network 40 formed by a LAN (Local Area Network) and the like. Note that the respective apparatuses need not always be connected via the network 40 as long as they can communicate with each other. For example, they can be connected to each other via USB (Universal Serial Bus), IEEE1394, or WAN (Wide Area Network).

In this case, the tomography apparatus (optical coherence tomography apparatus) 10 is implemented by, for example, a time-domain OCT or Fourier domain OCT, and has a function of capturing a tomographic image of the retina. The tomography apparatus 10 (OCT) obtains a plurality of tomographic images by one imaging operation, and sequentially arranges the tomographic images. This makes it possible to obtain a volume image (three-dimensional tomographic image) of the retina.

The tomography apparatus 10 captures tomographic images of an object (patient) and transmits the obtained volume image to the image display apparatus 20 in accordance with the operation by the user (technician or doctor). In some cases, this apparatus may transmit the volume image data to the data server 30.

The data server 30 has a function of storing various kinds of data. The data server 30 according to this embodiment stores the volume image of the retina captured by the tomography apparatus 10.

The image display apparatus 20 presents various kinds of information to the user. More specifically, the image display apparatus 20 displays the volume image captured by the tomography apparatus 10 or the volume image obtained from the data server 30 to the user.

Figure 2:
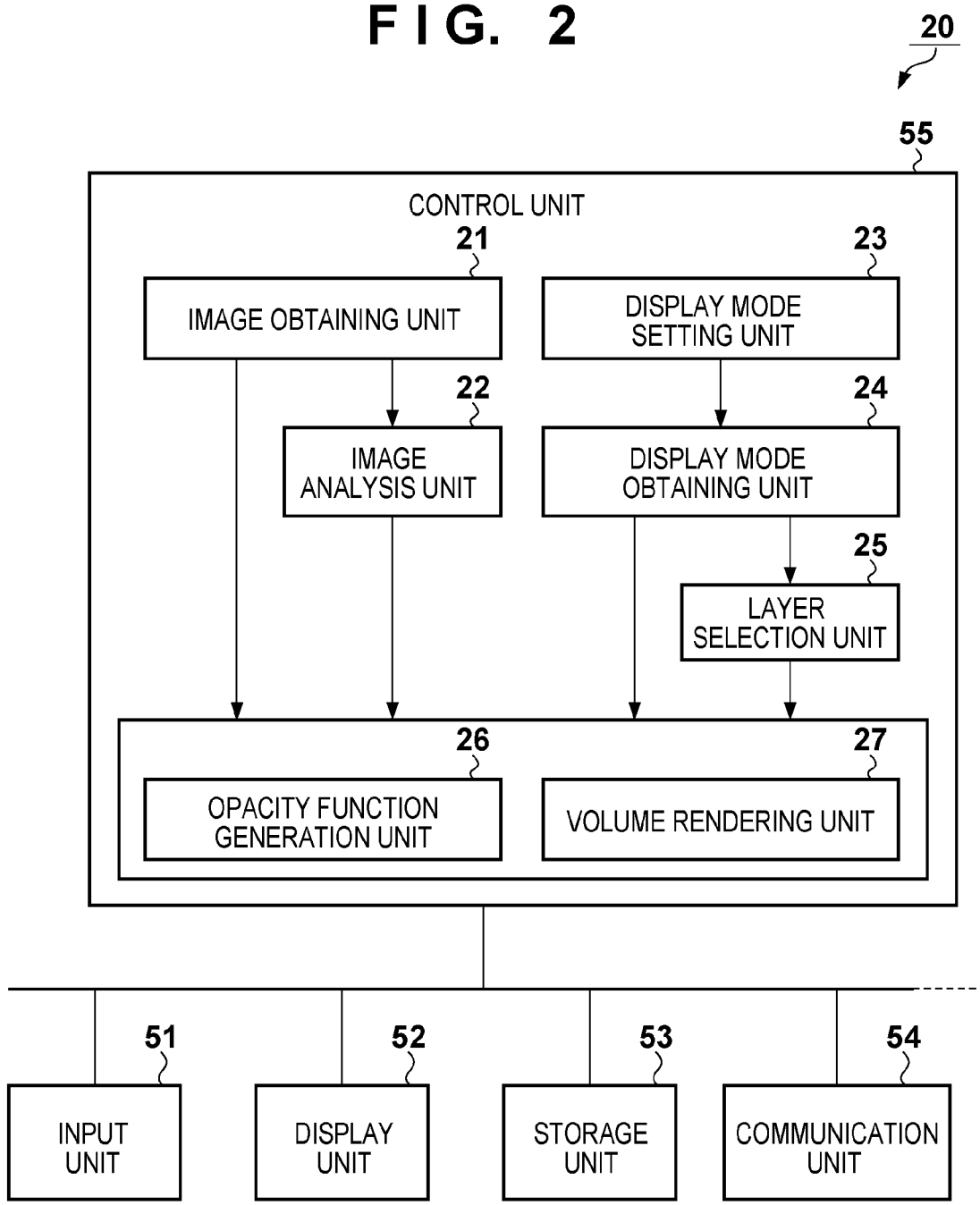
FIG. 2 is a block diagram showing an example of the functional arrangement of an image display apparatus 20 shown in FIG. 1.

An example of the functional arrangement of the image display apparatus 20 shown in FIG. 1 will be described next with reference to FIG. 2.

The image display apparatus 20 includes an input unit 51, a display unit 52, a storage unit 53, a communication unit 54, and a control unit 55, which constitute the functional arrangement of the image display apparatus 20.

The input unit 51 is implemented by, for example, a keyboard and a mouse, and inputs instructions from the user (doctor or technician) into the apparatus. The display unit 52 is implemented by, for example, a display such as a monitor, and displays various kinds of information to the user. Note that the display unit 52 may be provided outside the image display apparatus 20. That is, it is possible to use an information processing apparatus which performs display processing for an external display, instead of the image display apparatus. In addition, the input unit 51 and the display unit 52 may be implemented as a touch panel.

The storage unit 53 is implemented by, for example, a hard disk, and stores various kinds of information. The communication unit 54 is implemented by, for example, a network card, and exchanges various kinds of data with the tomography apparatus 10 and the data server 30. The control unit 55 is implemented by a CPU, ROM (Read Only Memory), and RAM (Random Access Memory), and comprehensively controls processing in the image display apparatus 20.

In this case, the control unit 55 includes an image obtaining unit 21, an image analysis unit 22, a display mode setting unit 23, a display mode obtaining unit 24, a layer selection unit 25, an opacity function generation unit 26, and a volume rendering unit 27. Note that each component in the control unit 55 is implemented by, for example, a CPU (Central Processing Unit) which reads out and executes programs stored in a ROM and the like.

The image obtaining unit 21 obtains the images captured by the tomography apparatus 10 and images stored in the data server via the communication unit 54 and the network 40. Note that the image obtaining unit 21 may directly obtain such images from an external storage medium (for example, a USB memory).

Figure 3:
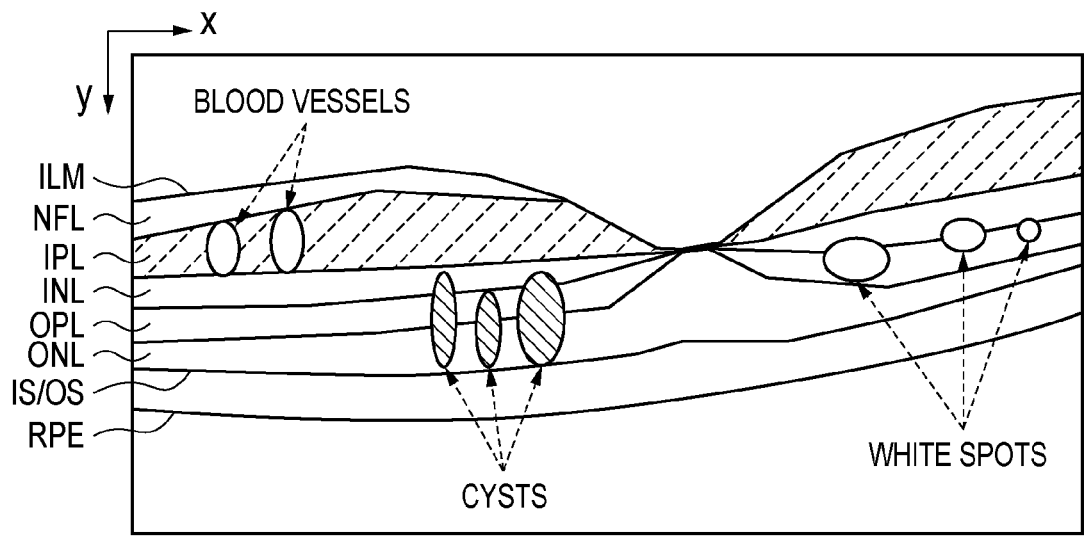
FIG. 3 is a schematic view showing an example of the layer structure of the retina.

The image analysis unit 22 analyzes the volume image obtained by the image obtaining unit 21. More specifically, the image analysis unit 22 analyzes the layer structure of the retina in the volume image (in the tomographic image of the retina), and extracts the boundary of each layer. In this processing, as shown in FIG. 3, the image analysis unit 22 extracts, for example, the inner limiting membrane (ILM), nerve fiber layer (NFL), inner plexiform layer (IPL), outer plexiform layer (OPL), inner nuclear layer (INL), outer nuclear layer (ONL), photoreceptor inner segment/outer segment (IS/OS) junction, and retinal pigment epithelium (RPE).

The display mode setting unit 23 sets a display mode based on an instruction from the user via the input unit 51. In this case, the display mode indicates a tissue as a display target in a volume image (in a tomographic image of the retina). A tissue as a display target includes, for example, a blood vessel, white spot, or cyst.

The display mode obtaining unit 24 obtains the display mode set by the display mode setting unit 23. Display modes include, for example, a blood vessel mode (in which a tissue as a display target is a blood vessel), a white spot mode (in which a tissue as a display target is a white spot), and a cyst mode (in which a tissue as a display target is a cyst). Obviously, it is possible to set other types of display modes.

The layer selection unit 25 selects a layer to be used to generate an opacity function based on the display mode set by the display mode setting unit 23 and the boundary of each layer extracted by the image analysis unit 22. If, for example, a tissue as a display target is a blood vessel (that is, the blood vessel mode), since the running of blood vessels are often seen in the inner plexiform layer (IPL), the layer selection unit 25 selects the IPL.

The opacity function generation unit 26 generates (different) opacity functions based on the layer selected by the layer selection unit 25. More specifically, the opacity function generation unit 26 generates an opacity function that assigns high opacities to voxels corresponding to the tissue as a display target and assigns low opacities to voxels corresponding to other tissues, based on the luminance values of a plurality of voxels in the layer selected by the layer selection unit 25. An opacity function is a function that changes a feature amount (for example, a luminance value) of each voxel into an opacity. For example, transparency is expressed by "0.0", and opacity is expressed by "1.0".

The volume rendering unit 27 performs volume rendering of a volume image on the display (input/output unit) by using the opacity function generated by the opacity function generation unit 26. This can provide display that allows the user to easily observe the tissue as a display target.

Figure 4:
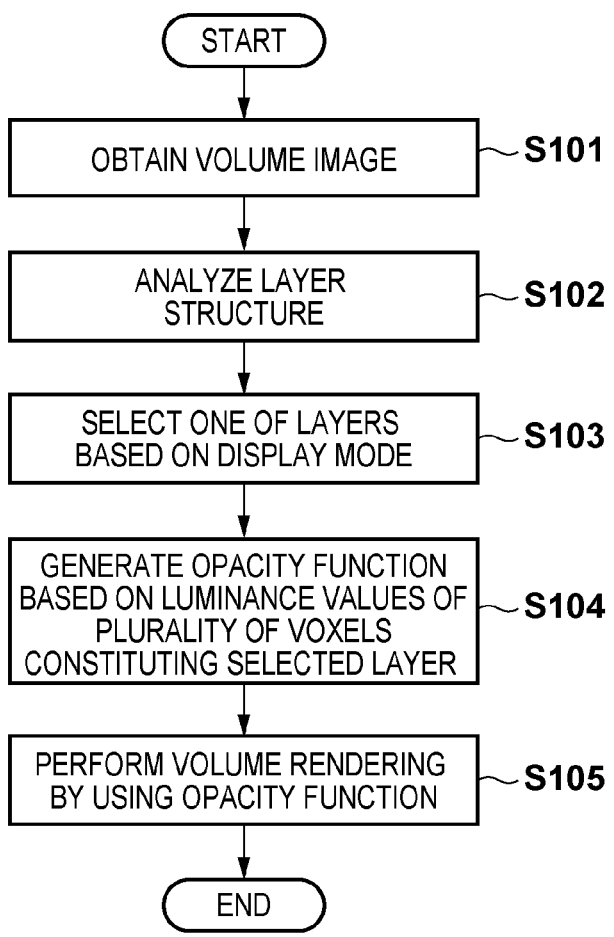
FIG. 4 is a flowchart showing an example of a processing procedure in the image display apparatus 20 shown in FIG. 1.

An example of a processing procedure in the image display apparatus 20 shown in FIG. 1 will be described next with reference to FIG. 4. The following will exemplify operation to be performed when the blood vessel mode (a tissue as a display target is a blood vessel) is set.

When starting this processing, first of all, the image display apparatus 20 causes the image obtaining unit 21 to obtain the volume image captured by the tomography apparatus 10 or a volume image stored in the data server 30 (S101). The image analysis unit 22 analyzes the layer structure of the retina in the obtained volume image and extracts the boundary of each layer (S102).

The image display apparatus 20 then causes the layer selection unit 25 to obtain the display mode designated by the user. The layer selection unit 25 selects a layer to be used to generate an opacity function in accordance with the obtained display mode (S103). When, for example, the user wants to display a blood vessel, he/she sets the blood vessel mode as a display mode. In this case, the layer selection unit 25 sets the IPL in the blood vessel mode because the running of blood vessels is often seen in the IPL.

Upon selection of a layer, the image display apparatus 20 causes the opacity function generation unit 26 to generate an opacity function necessary for volume rendering (S104). When generating an opacity function, first of all, the opacity function generation unit 26 generates a luminance value histogram of a plurality of voxels constituting the layer selected in the processing in step S103 and calculates the average value and standard deviation of the histogram. By using the calculated average value and standard deviation, the opacity function generation unit 26 generates an opacity function that makes voxels with lower luminance values become more transparent, and makes voxels with higher luminance values become more opaque.

In this case, since the blood vessel mode is set, the opacity function generation unit 26 generates a luminance value histogram of voxels in the IPL (see FIG. 5A), and calculates the average value and standard deviation of the histogram. Note that voxels in the IPL are those located between the lower end of the NFL and the lower end of the IPL which are obtained as an extraction result by the image analysis unit 22. In OCT, high luminance values appear in a region considered as a region in which a blood vessel runs. For this reason, it is thought that a large number of tissues other than blood vessels are distributed in a range in which luminance values are lower than a first reference value A (in this case, the average value) of the histogram shown in FIG. 5A. It is also thought that a large number of blood vessel tissues are distributed in the range of luminance values between the first reference value A (average value) and a second reference value B (average value+n×standard deviation).

Figure 5B:
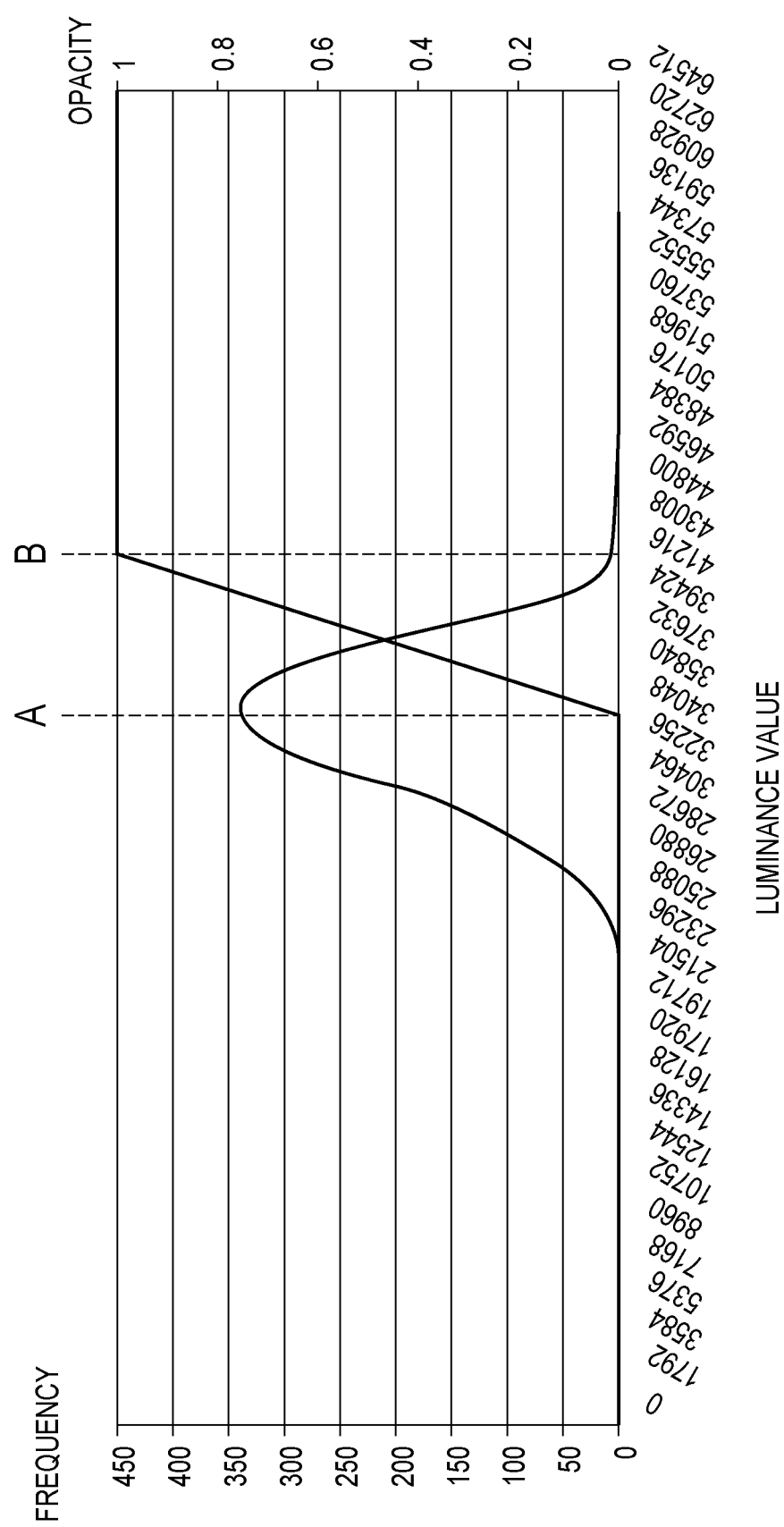
FIG. 5B is a graph showing an example of an opacity function.

To display the information between A and B so as to facilitate observation of the information, the opacity function generation unit 26 generates the opacity function shown in FIG. 5B. More specifically, the opacity function generation unit 26 generates an opacity function that makes regions (voxels) with luminance values equal to or less than the first reference value (average value) transparent and makes regions with luminance values exceeding the second reference value (average value+n×standard deviation) opaque. In addition, this opacity function is configured to increase the opacity with an increase in luminance value between A and B. That is, voxels having luminance values between A and B are processed into translucent voxels. In this case, the value n has a function of controlling the range of luminance values in which voxels are made translucent.

According to an example of the opacity function shown in FIG. 5B, the manner of changes in opacity is indicated as linear. Obviously, the apparatus may be configured to generate a nonlinear function such as a quadratic function. Using a quadratic function will assign lower opacities to regions with lower luminance values and assigns higher opacities to regions with higher luminance values. This can display a blood vessel region with higher contrast.

The image display apparatus 20 then causes the volume rendering unit 27 to perform volume rendering of the volume image (S105). The volume rendering unit 27 performs this processing by using the layer extraction result in step S102, the opacity function generated in step S104, and the layer selected in step S103. As a volume rendering algorithm, a generally known volume ray casting method can be used. Note, however, that target voxels from which opacities are calculated based on luminance values are voxels in a layer selected based on the blood vessel mode. Voxels other than the target voxels are assigned with the opacity "0.0", that is, are made transparent.

Figure 6A:
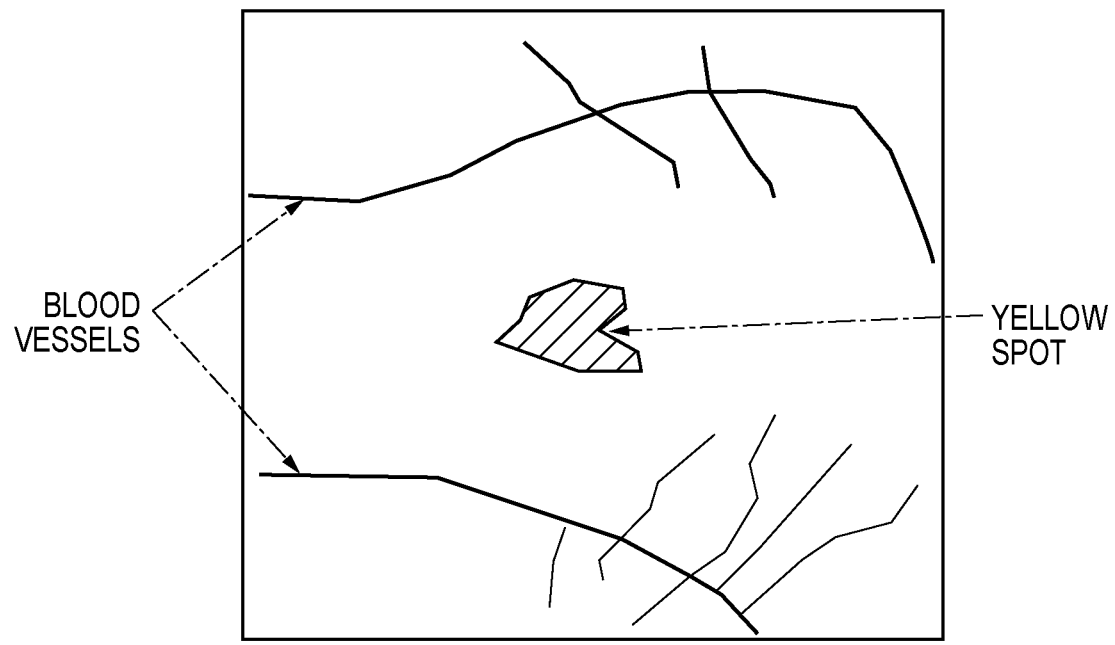
FIGS. 6A and 6B are views showing an example of a display form.

As described above, according to this embodiment, when, for example, the user has selected the blood vessel mode, this apparatus automatically generates an opacity function that assigns high opacities to blood vessel tissues and assigns low opacities to tissues other than the blood vessel tissues. Performing volume rendering by using this opacity function can present the display shown in FIG. 6A to the user. This allows the user to easily observe three-dimensional running of blood vessels running in the retinal layer. Note that FIG. 6A is a schematic view displaying three-dimensional running of blood vessels viewed from above (y direction) the retina shown in FIG. 3.

(Second Embodiment)

The second embodiment will be described next. The second embodiment will exemplify operation to be performed upon setting of the white spot mode of performing volume rendering of a three-dimensional distribution of white spots. Note that since the arrangements of a diagnosis support system and image display apparatus 20 according to the second embodiment are the same as those shown in FIGS. 1 and 2, with reference to which the first embodiment has been described, a description of them will be omitted. Different processes from those in the first embodiment will be mainly described with reference to the flowchart of FIG. 4, with reference to which the first embodiment has been described.

The image display apparatus 20 obtains a volume image, and then analyzes the volume image as in the first embodiment described above (steps S101 and S102).

In this case, if the white spot mode is set, the image display apparatus 20 causes a layer selection unit 25 to select the layer located between the lower end of the NFL and the IS/OS because a large number of white spots are distributed in the layer between them (S103).

The image display apparatus 20 then causes an opacity function generation unit 26 to generate a luminance value histogram of a plurality of voxels constituting the layer selected in the processing in step S103, and calculates the average value and standard deviation of the histogram. By using the calculated average value and standard deviation, the opacity function generation unit 26 generates an opacity function that makes voxels with lower luminance values become more transparent, and makes voxels with higher luminance values become more opaque (S104). Note that the voxels used to generate the luminance value histogram are those located between the lower end of the NFL and IS/OS. In OCT, the luminance value of a white spot is high. For this reason, it is thought that in the luminance value histogram, a large number of white spots are distributed in the range of high luminance values, and a large number of tissues other than the white spots are distributed in the range of low luminance values. The opacity function generation unit 26 generates an opacity function that makes voxels with luminance values equal to or less than a first reference value A (average value) transparent and makes voxels with luminance values exceeding a second reference value B (average value+n× standard deviation) opaque as in the first embodiment. In addition, the opacity function generation unit 26 generates an opacity function that changes the opacities of voxels having luminance values between the reference values A and B as in the first embodiment.

The image display apparatus 20 then causes a volume rendering unit 27 to perform volume rendering of the volume image as in the first embodiment (S105). In this case, assume that voxels for which opacities are to be calculated from luminance values are those in the layer selected based on the white spot mode. Voxels other than the target voxels are assigned with the opacity "0.0", that is, are made transparent.

Figure 6B:
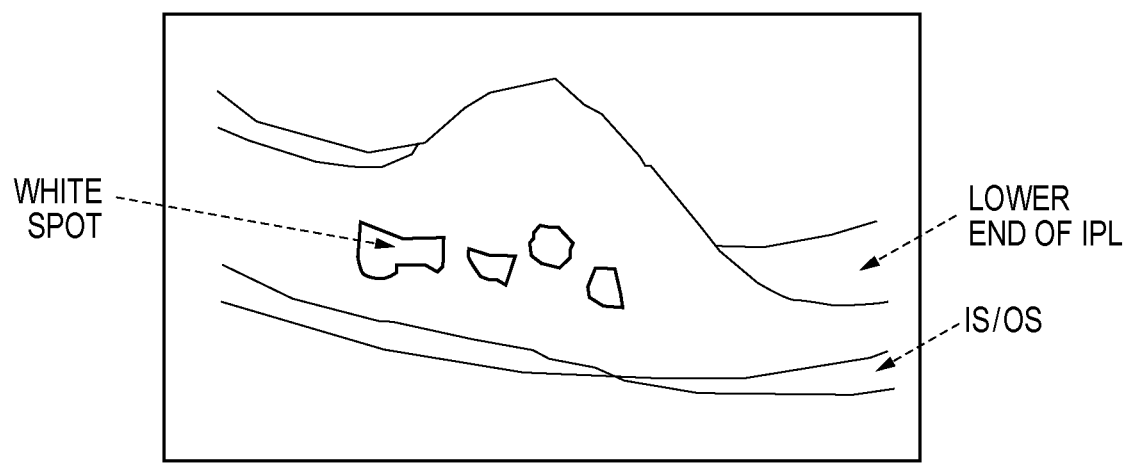

As described above, according to the second embodiment, when the user has selected the white spot mode, this apparatus automatically generates an opacity function that assigns high opacities to white spot tissues, and assigns low opacities to tissues other than the white spot tissues. Performing volume rendering by using this opacity function can present the display shown in FIG. 6B to the user. This allows the user to easily observe three-dimensional distributions of white spots and high-luminance tissues in the retinal layer.

(Third Embodiment)

The third embodiment will be described next. The third embodiment will exemplify operation to be performed when performing volume rendering of a three-dimensional distribution of cysts. Note that since the arrangements of a diagnosis support system and image display apparatus 20 according to the third embodiment are the same as those shown in FIGS. 1 and 2, with reference to which the first embodiment has been described, a description of them will be omitted. Different processes from those in the first embodiment will be mainly described with reference to the flowchart of FIG. 4, with reference to which the first embodiment has been described.

When the white spot mode or the blood vessel mode is set, this apparatus generates an opacity function that assigns high opacities to regions (voxels) with high luminance values, and assigns low opacities to regions with low luminance values. In contrast to this, in the cyst mode, when performing OCT, the apparatus generates an opacity function that assigns high opacities to regions with low luminance values, and assigns low opacities to regions with high luminance values, because cyst regions have low luminance values.

If the cyst mode is set, the image display apparatus 20 causes a layer selection unit 25 to select at least one of the INL, OPL, and ONL because a large number of cysts are distributed in them (S103).

The image display apparatus 20 then causes an opacity function generation unit 26 to generate a luminance value histogram of a plurality of voxels constituting the layer selected in the processing in step S103, and calculates the average value and standard deviation of the histogram. By using the calculated average value and standard deviation, the opacity function generation unit 26 generates an opacity function that makes voxels with lower luminance values become more transparent, and makes voxels with higher luminance values become more opaque (S104). Note that the voxels used to generate a luminance value histogram are those located between the upper boundary of the INL and the lower boundary of the ONL. As described above, since the luminance value of a cyst region is low, it is necessary to display the region with low luminance so as to facilitate observation of the region.

Figure 7A:
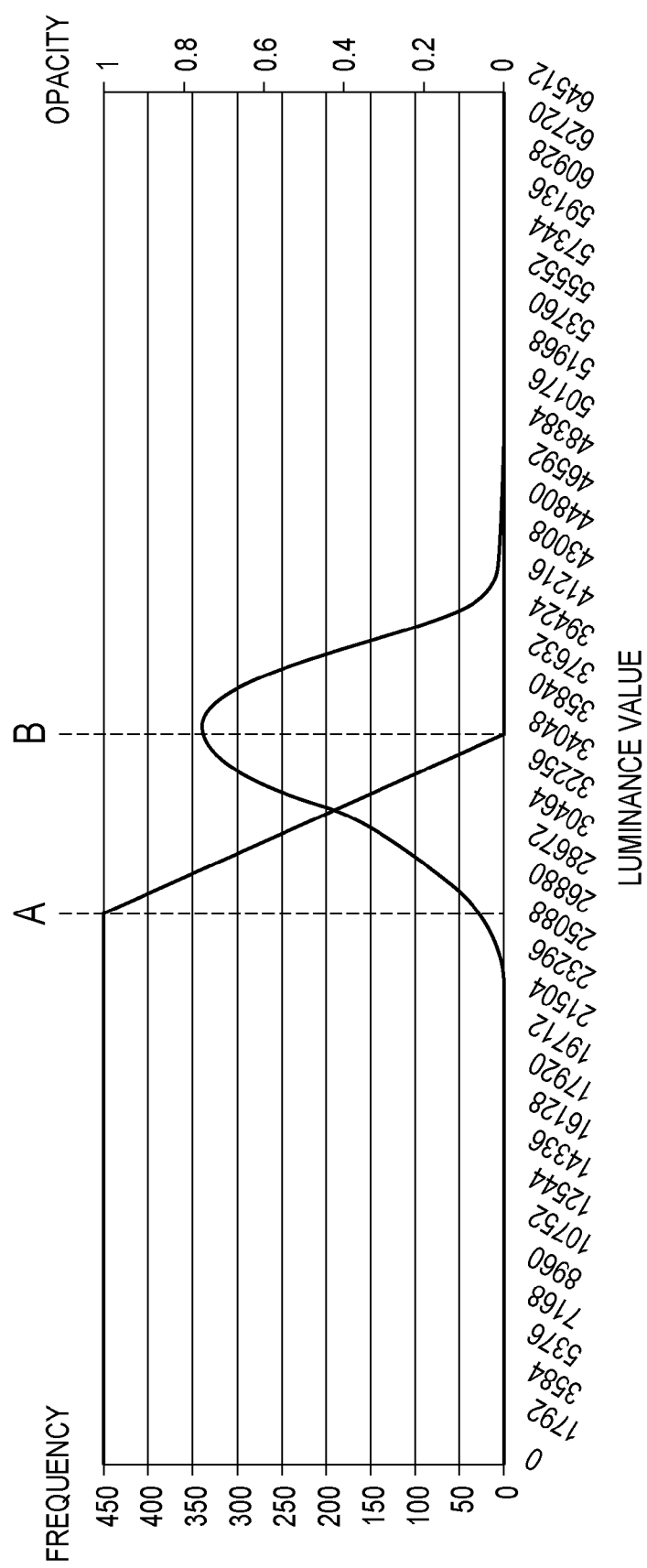
FIG. 7A is a graph showing an example of an opacity function according to the third embodiment.

As shown in FIG. 7A, the opacity function generation unit 26 therefore generates an opacity function that makes voxels with luminance values equal to or less than a first reference value A (in this case, average value−n×standard deviation) opaque, and makes voxels with luminance values exceeding a second reference value B (average value) transparent. This opacity function is also configured to assign lower opacities to voxels with luminance values between A and B (voxels having luminance values which exceed the first reference value and are equal to or less than the second reference value) with an increase in luminance value. That is, voxels having luminance values between A and B are processed into translucent voxels. As in the above case, the value n has a function of controlling the range of luminance values in which voxels are made translucent.

The image display apparatus 20 then causes the volume rendering unit 27 to perform volume rendering of a volume image as in the first embodiment (S105).

Figure 7B:
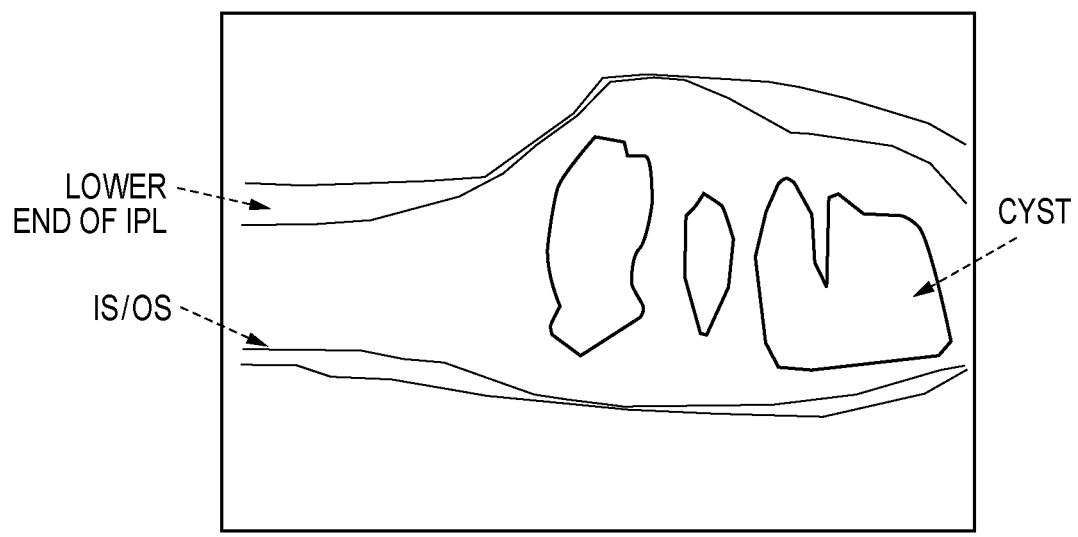
FIG. 7B is a view showing an example of a display form according to the third embodiment.

As described above, according to the third embodiment, when the user has selected the cyst mode, this apparatus automatically generates an opacity function that assigns high opacities to white cyst tissues, and assigns low opacities to tissues other than the cyst tissues. Performing volume rendering by using this opacity function can present the display shown in FIG. 7B to the user. This allows the user to easily observe three-dimensional distributions of cysts and high-luminance tissues in the retinal layer.

The typical embodiments of the present invention have been described above. However, the present invention is not limited to the embodiments described above and shown in the accompanying drawings, and can be modified and executed as needed within the spirit and scope of the invention.

For example, tissues as display targets in a tomographic image of the retina may be the entire retina. In this case, the image display apparatus 20 generates an opacity function from the voxels in the entire retinal layer, and performs volume rendering by using the opacity function. This makes it possible to automatically display the entire retina so as to facilitate observation of the retina.

As has been described above, according to the present invention, an opacity function is automatically generated in accordance with a display target. This makes it possible to perform volume rendering that allows the user to easily observe a tissue as a display target, thereby improving diagnosis accuracy.

(Other Embodiments)

Aspects of the present invention can also be realized by a computer of a system or apparatus (or devices such as a CPU or MPU) that reads out and executes a program recorded on a memory device to perform the functions of the above-described embodiment(s), and by a method, the steps of which are performed by a computer of a system or apparatus by, for example, reading out and executing a program recorded on a memory device to perform the functions of the above-described embodiment(s). For this purpose, the program is provided to the computer for example via a network or from a recording medium of various types serving as the memory device (for example, computer-readable storage medium).

While the present invention has been described with reference to exemplary embodiments, it is to be understood that the invention is not limited to the disclosed exemplary embodiments. The scope of the following claims is to be accorded the broadest interpretation so as to encompass all such modifications and equivalent structures and functions.

This application claims the benefit of Japanese Patent Application No. 2010-219765 filed on Sep. 29, 2010, which is hereby incorporated by reference herein in its entirety.

What is claimed is:

1. A processing apparatus comprising:
an analysis unit configured to analyze a layer structure of a three-dimensional tomographic image of a retina acquired by an optical coherence tomography apparatus;
a selection unit configured to select a display target other than the analyzed layer structure in a retina; and
a generation unit configured to generate an opacity function indicating an opacity of a plurality of voxels constituting a region corresponding to the selected display target in a three-dimensional tomographic image of the retina, based on the selected display target and a frequency distribution of luminance values of the plurality of voxels.

2. The apparatus according to claim 1, wherein said generation unit generates, based on the selected display target, an opacity function that indicates higher or lower opacities for voxels, which have luminance values higher than a predetermined value, than for other voxels among the plurality of voxels.

3. The apparatus according to claim 1, further comprising:
a volume rendering unit configured to perform volume rendering of the region based on the opacity function; and
a display control unit configured to cause a display unit to display an image having undergone the volume rendering.

4. The apparatus according to claim 1, wherein the selection unit selects at least one of layers corresponding to the selected display target as the region, and
wherein the generation unit generates the opacity function based on the selected display target and a frequency distribution of luminance values of the plurality of voxels constituting the selected layers.

5. The apparatus according to claim 4, further comprising a setting unit configured to set a display mode indicating the display target,
wherein the selection unit selects, in accordance with the set display mode, the at least one of layers as the region.

6. The apparatus according to claim 1, wherein the selection unit selects an inner plexiform layer as the region when a blood vessel is selected as the display target, and
wherein the generation unit generates, based on a frequency distribution of luminance values of the plurality of voxels constituting the selected inner plexiform layer, an opacity function that indicates higher opacities for voxels, which have luminance values higher than a predetermined value, than for other voxels among the plurality of voxels.

7. The apparatus according to claim 1, wherein the selection unit selects layers between a lower end of a nerve fiber layer and a retinal pigment epithelium as the region when a white spot is selected as the display target, and
wherein the generation unit generates, based on a frequency distribution of luminance values of the plurality of voxels constituting the selected layers, an opacity function that indicates higher opacities for voxels, which have luminance values higher than a predetermined value, than for other voxels among the plurality of voxels.

8. The apparatus according to claim 1, wherein the selection unit selects an inner nuclear layer, an external pexiform layer, and an outer nuclear layer as the region when a cyst is selected as the display target, and
wherein the generation unit generates, based on a frequency distribution of luminance values of the plurality of voxels constituting the selected layers, an opacity function that indicates lower opacities for voxels, which have luminance values higher than a predetermined value, than for other voxels among the plurality of voxels.

9. The apparatus according to claim 1, wherein said generation unit (a) calculates a first reference value for luminance values of the plurality of voxels and a second reference value indicating a larger value than the first reference value by using an average value and standard deviation calculated based on the luminance values, and (b) generates an opacity function that makes a voxel having a luminance value not more than the first reference value transparent, makes a voxel having a luminance value exceeding the second reference value opaque, and increases an opacity of a voxel having a luminance value which exceeds the first reference value and is not more than the second reference value, with an increase in luminance value from the first reference value to the second reference value.

10. The apparatus according to claim 4, wherein said generation unit (a) calculates a first reference value for luminance values of the plurality of voxels in the selected layers and a second reference value indicating a larger value than the first reference value by using an average value and standard deviation calculated based on the luminance values, and (b) generates an opacity function that makes a voxel having a luminance value not more than the first reference value opaque, makes a voxel having a luminance value exceeding the second reference value transparent, and increases a transparency of a voxel having a luminance value which exceeds the first reference value and is not more than the second reference value, with an increase in luminance value from the first reference value to the second reference value.

11. A processing method comprising:
analyzing a layer structure of a three-dimensional tomographic image of a retina acquired by an optical coherence tomography apparatus;
selecting a display target other than the analyzed layer structure in a retina; and
generating an opacity function indicating an opacity of a plurality of voxels constituting a region corresponding to the selected display target in a three-dimensional tomographic image of the retina, based on the selected display target and a frequency distribution of luminance values of the plurality of voxels.

12. The method according to claim 11, wherein in said step of generating, based on the selected display target, an opacity function is generated that indicates higher or lower opacities for voxels, which have luminance values higher than a predetermined value, than for other voxels among the plurality of voxels.

13. The method according to claim 11, further comprising:
performing volume rendering of the region based on the opacity function; and
causing a display unit to display an image having undergone the volume rendering.

14. The method according to claim 11, wherein in the step of selecting, at least one of layers corresponding to the selected display target are selected as the region, and
wherein in the step of generating, the opacity function is generated based on the selected display target and a frequency distribution of luminance values of the plurality of voxels constituting the selected layers.

15. The method according to claim 14, further comprising setting a display mode indicating the display target,
wherein in the step of selecting, in accordance with the set display mode, the at least one of layers are selected as the region.

16. The method according to claim 11, wherein in the step of selecting, an inner plexiform layer is selected as the region when a blood vessel is selected as the display target, and
wherein in the step of generating, based on a frequency distribution of luminance values of the plurality of voxels constituting the selected inner plexiform layer, an opacity function is generated that indicates higher opacities for voxels, which have luminance values higher than a predetermined value, than for other voxels among the plurality of voxels.

17. The method according to claim 11, wherein in the step of selecting, layers between a lower end of a nerve fiber layer and a retinal pigment epithelium are selected as the region when a white spot is selected as the display target, and wherein in the step of generating, based on a frequency distribution of luminance values of the plurality of voxels constituting the selected layers, an opacity function is generated that indicates higher opacities for voxels, which have luminance values higher than a predetermined value, than for other voxels among the plurality of voxels.

18. The method according to claim 11, wherein in the step of selecting, an inner nuclear layer, an external pexiform layer, and an outer nuclear layer are selected as the region when a cyst is selected as the display target, and
wherein in the step of generating, based on a frequency distribution of luminance values of the plurality of voxels constituting the selected layers, an opacity function is generated that indicates lower opacities for voxels, which have luminance values higher than a predetermined value, than for other voxels among the plurality of voxels.

19. A non-transitory computer-readable storage medium storing a program for causing a computer to execute each step of a processing method defined in claim 11.

20. A medical system comprising:
an analysis unit configured to analyze a layer structure of a three-dimensional tomographic image of a retina acquired by an optical coherence tomography apparatus;
a layer selection unit configured to select at least one layer of layers in the three-dimensional tomographic image of the retina by using the analyzed layer structure based on a display target other than the analyzed layer structure in the three-dimensional tomographic image of the retina;
a generation unit configured to generate an opacity function indicating an opacity of each of a plurality of voxels constituting the selected layer, based on a frequency distribution of luminance values of the plurality of voxels; and
a volume rendering unit configured to perform volume rendering of the three-dimensional tomographic image of the retina based on the opacity function.

21. A processing apparatus comprising:
an analysis unit configured to analyze a layer structure of a three-dimensional tomographic image of a retina acquired by an optical coherence tomography apparatus;
a layer selection unit configured to select at least one layer of layers in the three-dimensional tomographic image of the retina by using the analyzed layer structure based on a display target other than the analyzed layer structure in the three-dimensional tomographic image of the retina;
a generation unit configured to generate an opacity function indicating an opacity of each of a plurality of voxels constituting the selected layer, based on a frequency distribution of luminance values of the plurality of voxels; and
a volume rendering unit configured to perform volume rendering of the three-dimensional tomographic image of the retina based on the opacity function.

22. A processing method comprising:
analyzing a layer structure of a three-dimensional tomographic image of a retina acquired by an optical coherence tomography apparatus;
selecting at least one layer of layers in the three-dimensional tomographic image of the retina by using the analyzed layer structure based on a display target other than the analyzed layer structure in the three-dimensional tomographic image of the retina;
generating an opacity function indicating an opacity of each of a plurality of voxels constituting the selected layer, based on a frequency distribution of luminance values of the plurality of voxels; and
performing volume rendering of the three-dimensional tomographic image of the retina based on the opacity function.

23. A non-transitory computer-readable storage medium storing a program for causing a computer to execute each step of a processing method defined in claim 22.

24. A processing apparatus comprising:
an analysis unit configured to analyze a layer structure of a three-dimensional tomographic image of a retina acquired by an optical coherence tomography apparatus;
a layer selection unit configured to select at least one layer of layers in the three-dimensional tomographic image of the retina by using the analyzed layer structure; and
a volume rendering unit configured to perform volume rendering of the three-dimensional tomographic image of the retina based on an opacity function indicating an opacity of a plurality of voxels constituting the selected layer.

25. A processing method comprising:
analyzing a layer structure of a three-dimensional tomographic image of a retina acquired by an optical coherence tomography apparatus;
selecting at least one layer of layers in the three-dimensional tomographic image of the retina by using the analyzed layer structure; and
performing volume rendering of the three-dimensional tomographic image of the retina based on an opacity function indicating an opacity of a plurality of voxels constituting the selected layer.

26. A non-transitory computer-readable storage medium storing a program for causing a computer to execute each step of a processing method defined in claim 25.

* * * * *